United States Patent [19]
Okamoto et al.

[11] 4,397,678
[45] Aug. 9, 1983

[54] PLANT GROWTH REGULATORS

[75] Inventors: Toshihiko Okamoto, 1-7-19,, Shinoharakita, Kohokuku, Yokohamashi, Kanagawa; Yo Isogai, 1-1-2-609, Kamiyoga, Setagayaku, Tokyo; Koichi Shudo, 2000-10-2-116, Kosugayacho, Totsukaku, Yokohamashi, Kanagawa, all of Japan; Soshiro Takahashi, Saitama, Japan

[73] Assignees: Toshihiko Okamoto, Kanagawa; Yo Isogai, Tokyo; Koichi Shudo, Kanagawa; Susumu Sato, Saitama, all of Japan

[21] Appl. No.: 343,090

[22] Filed: Jan. 27, 1982

Related U.S. Application Data

[62] Division of Ser. No. 154,664, May 30, 1980, Pat. No. 4,331,807.

[30] Foreign Application Priority Data

May 31, 1979 [JP] Japan ................................ 54-67872

[51] Int. Cl.$^3$ ............................................. A01N 43/58
[52] U.S. Cl. ........................................... 71/72; 71/74; 71/76
[58] Field of Search ................................ 71/92, 76, 74

[56] References Cited

U.S. PATENT DOCUMENTS 4,193,788  3/1980  Shudo et al. ............................ 71/94

OTHER PUBLICATIONS

Okamoto et al., Chem. Abst., vol. 87, (1974) 178867.

Primary Examiner—Catherine L. Mills
Attorney, Agent, or Firm—Sughrue, Mion, Zinn, Macpeak & Seas

[57] ABSTRACT

Plant growth regulators of the N-(4-pyridazinyl)urea and thiourea type are disclosed which exhibit excellent cytokinin-like activities and are useful for regulating plant growth in various manners, such as acceleration and suppression.

4 Claims, No Drawings

PLANT GROWTH REGULATORS

This is a division of application Ser. No. 154,664, filed May 30, 1980, now U.S. Pat. No. 4,331,807.

BACKGROUND OF THE INVENTION

1. Field of the Invention

This invention relates to novel N-(4-pyridazinyl)-N'-phenylureas and -phenylthioureas (often referred to as N-(4-pyridazinyl)-N'-phenylureas), agricultural composition comprising such as an active ingredient(s) and methods of treating plants therewith.

2. Description of the Prior Art

In the agricultural and horticultural fields, increasing attention has been directed to plant growth regulators which accelerate or suppress the growth of plants.

In particular, recently techniques for controlling plant growth utilizing the hormone activity of chemicals such as cytokinin or gibberellin have been investigated. Plant growth regulators exhibiting cytokinin-like hormonal activity (hereafter referred to as cytokinin hormone activity) can regulate plant growth when used in vary small amounts. On the other hand, plant growth can sometimes be suppressed when such chemicals are employed in high amounts, i.e., in amounts over those effective to accelerate plant growth (sometimes referred to as overdose use).

Accordingly, while the terms "plant growth regulation" and "plant growth regulator" used herein refer primarily to acceleration, they sometimes refer to the suppression of plant growth in a broad sense. Such seemingly contrary activities by the plant growth regulator are characteristic of cytokinin activity. In this regard, herbicides for which cytokinin activity has clearly been established are not known, though some herbicides have been established to have auxin activity.

Typical plant growth regulators known as having cytokinin hormone activity are 6-benzyladenine, kinetin, and N-(4-pyridyl)-N'-phenylurea. Of these, N-(4-pyridyl)-N'-phenylurea is disclosed in British Pat. No. 1,122,662 as a representative of N-heterocyclic aromatic-N'-aryl ureas which may be substituted by halogen, alkyl or nitro at the heterocyclic aryl moiety. The present inventors have previously found that N-(4-pyridyl)-N'-phenylureas having specific substituents such as halogen atoms are potent plant growth regulators when the substitution occurs at the 2-position of the 4-pyridyl moiety and filed as Ser. No. 947,468 dated Oct. 2, 1978 now U.S. Pat. No. 4,193,788.

Despite the above, the development of plant growth regulators having more improved effects is still desired by the art.

SUMMARY OF THE INVENTION

It has been found that ureas containing a pyridazine ring, i.e., N-(4-pyridazinyl)-N'-phenylureas, possess strong or potent cytolinin hormone activities.

An object of this invention is thus to provide novel plant growth regulators which provide effects equivalent to or superior to known plant growth regulators, agricultural compositions comprising the same and methods of controlling plant growth using the same.

The plant growth regulator of this invention can accelerate or suppress the growth of plants as described above to regulate plants to any desired degree.

Thus the plant growth regulators of the invention have a wide variety of practical features, e.g., not only can they promote or suppress the weight, height or yield of plants, but they also insure flowering or fruiting at a desired time, the formation of seedless fruit, maintain seeds in a dormant state or conversely arouse seeds from a dormant state, prevent flowering or fruit plants and trees from shedding, prevent leaves from defoliating, preserve the freshness of plants or harvested plants, etc.

DETAILED DESCRIPTION OF THE INVENTION

The compounds of the invention are N-(4-pyridazinyl)-N'-phenylureas represented by the following formula (I):

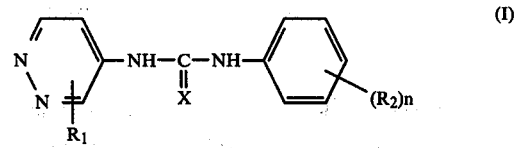

wherein $R_1$ and $R_2$, which may be the same or different, each represents a hydrogen atom, a lower alkyl group (preferably an alkyl group having 1 to about 4 carbon atoms), a halogen atom (preferably a chlorin, bromine or fluorine atom), a lower alkoxy group (preferably an alkoxy group having 1 to about 4 carbon atoms), an aryloxy group (preferably having 6 carbon atoms, e.g., a phenoxy group), a halomethyl group (preferably a trifluoromethyl group), a cyano group, an alkylthio group (preferably having a 1 to 4 carbon atom alkyl substituent, a carboxy or alkoxycarbonyl group (preferably having a 1 to 4 carbon atom alkyl moiety); X represents an oxygen atom or a sulfur atom; and n represents 1, 2 or 3; when n represents 2 or 3, the $R_2$ moieties may be different.

Representative examples of such ureas include N-(4-pyridazinyl)-N'-phenylurea, N-(4-pyridazinyl)-N'-(m-chlorophenyl)urea, N-(4-pyridazinyl)-N'-(m-fluorophenyl)urea, N-(4-pyridazinyl)-N'-(m-trifluoromethylphenyl)urea, N-(4-pyridazinyl)-N'-(m-cyanophenyl)urea, N-(6-methyl-4-pyridazinyl)-N'-phenylurea, N-(4-pyridazinyl)-N'-phenylthiourea, N-(6-chloro-4-pyridazinyl)-N'-phenylurea, N-(6-chloro-4-pyridazinyl)-N'-(m-chlorophenyl)urea, N-(6-chloro-4-pyridazinyl)-N'-(m-fluorophenyl)urea, etc.

Of the ureas represented by formula(I) above, compounds wherein $R_1$ is a hydrogen atom, a chlorine atom or a methoxy group; $R_2$ is a hydrogen atom, a chlorine atom or a fluorine atom; n is 1; and X is an oxygen atom, e.g., N-(4-pyridazinyl)-N'-phenylurea, N-(4-pyridazinyl)-N'-(m-fluoro- or -chlorophenyl)urea, N-(6-methyl-4-pyridazinyl)-N'-phenylurea, etc., are particularly preferred in the invention.

The compounds of the invention -N-(4-pyridazinyl)-N'-phenylureas and -phenylthioureas- are superior plant growth regulators to benzyladenine, N-(4-pyridyl)-N'-phenylurea and N-(2-chloro-4-pyridyl)-N'-phenylurea which are known potent plant growth regulators.

The compounds of the invention, N-(4-pyridazinyl)-N'-phenylureas (I), can be synthesized as follows.

(a) N-(4-pyridazinyl)-N'-phenylureas (I) can be prepared by the reaction of 4-aminopyridazines (II) and phenyliso(thio)cyanates (III) according to the following reaction equation:

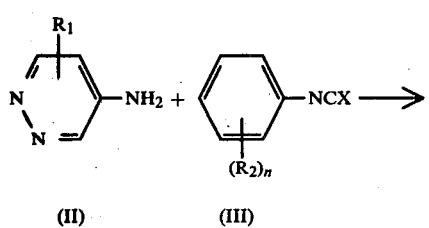

(II)  (III)

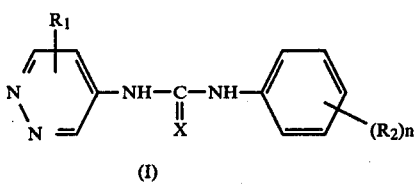

(I)

wherein $R_1$, $R_2$, n and X are as defined above.

(b) Compounds of formula(I) can also be prepared by the reaction of pyridazinyl isocyanates (IV) and anilines (V) according to the following reaction equation.

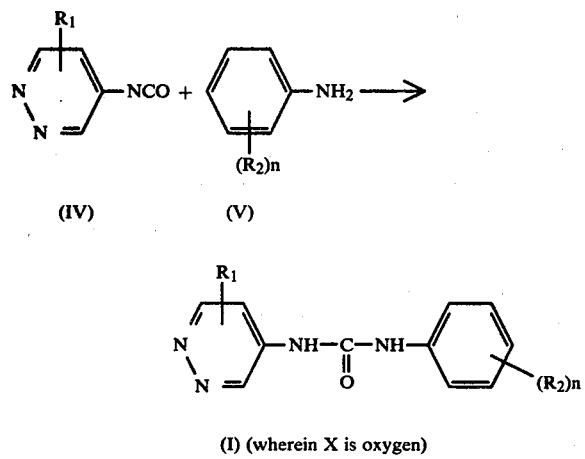

(I) (wherein X is oxygen)

wherein $R_1$, $R_2$ and n are as defined above.

Reactions (a) and (b) can be performed in a solvent inert to amines (II, V) or iso(thio)cyanates (III, IV) or in the absence of a solvent, at room temperature or under heating at temperatures of $-10°$ to $150°$ C., preferably $10°$ to $60°$ C., for a reaction time of about 1 min. to 2 days, preferably 30 mins. to about 3 hours, under normal pressure. Typical examples of such inert solvents are benzene, ethyl acetate, acetone, pyridine, dioxiane, etc., which are particularly preferably used in reactions (a) and (b). If the starting materials are used in excess, they also function as a reaction solvent.

The iso(thio)cyanates (III, IV) can be formed by pyrolysis (at about 50° to about 150° C.) of the corresponding acid azides shown by formulae (VI) and (VII):

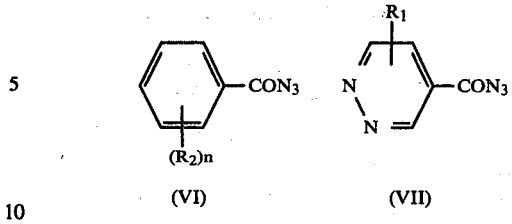

(VI)  (VII)

wherein $R_1$, $R_2$ and n are the same as defined above, in a reaction solvent such as an inert solvent, e.g., benzene, toluene, etc.

The thus formed product can be reacted with an amine as it is, without isolating the same, and, therefore, the acid azides (VI, VII) are also advantageous for producing the compounds of the invention.

Hydrolysis, acylation or esterification can then be performed to convert the substituents in the reaction products obtained either of the reactions above into other desired substituents in a conventional manner. These reactions are generally performed under the following reaction conditions.

Temperature: $-10°$ to $150°$ C., preferably $10°$ to $60°$ C.

Time: 1 min. to 2 days, preferably 30 mins. to about 3 hours.

Solvent: in an inert solvent such as benzene, toluene, ethyle acetate, pyridine, acetone or dioxane.

Pressure: normal pressure

Of compounds mentioned above, 4-aminopyridazines (II) can also be prepared in a conventional manner, e.g., by reducing the corresponding 4-nitropyridazines or 4-nitropyridazine-1-oxides with metals (e.g., Fe), or by subjecting these compounds to catalytic hydrogenation.

Other compounds than those indicating preparations thereof as above are all commercially available.

The N-(4-pyridazinyl)-N'-phenylureas in accordance with the invention exhibit excellent biological activity on plants equivalent to that of benzyladenine or 4-pyridylphenylureas, but at a much lower concentration, in particular, an excellent accelerating action on cell mitosis, cell enlargement, cell differentiation, etc.; and are effective in accelerating fruiting, preventing fruit and flowers from falling, growth acceleration, weight increase of leaves, stalks, etc., retarding senescenece, preventing injury due to freezing or low temperatures, etc.

In addition, at higher concentrations, a marked suppression of growth (i.e., herbicidal activity) is exhibited, and, for example, the compounds of the invention can also be employed as herbicides.

The compounds of this invention are particularly effective, based on the above biological activities, in accelerating fruit on pepos such as melons, water melons, etc., in preventing flower shedding in grapevines, in accelerating the growth of vegetables, in increasing the size of the tobacco leaf, in regulating the composition or ingredients (such as alkaloids, sugar, etc.) of plants, etc.

When compared with 6-benzyladenine or kinetin which are known to be the most potent plant growth regulators, the compounds of the invention exhibit the same level of activity at a concentration 1/10 to 1/100 that of the known compounds. When compared with N-(4-pyridyl)-N'-phenylurea, the activity of the compounds of this invention is 1000 times or more the activity thereof. In addition, the compounds of the invention exhibit at least 10 times the effects of N-(2-chloro-4-pyridyl)-N'-phenylurea previously disclosed by the present inventors. Furthermore, the compounds of the invention exhibit at least 10,000 times the effects of N-(4-pyrimidyl)-N'-phenylureas disclosed in British Pat. No. 1,122,662.

More specifically, the optimal concentration for giving the highest yield of tobacco callus in cell mitosis acceleration testing on tobacco callus was as shown below:

| Compound | Optimal Concentration (ppm) |
|---|---|
| 6-Benzyladenine | 0.01 |
| N—(4-Pyridyl)-N'—phenylurea | 0.1 |
| N—(4-Pyridazinyl)-N'—phenylureas | 0.00005–0.001 |

The optimal concentration of 6-benzyladenine is 10 ppm in callus shoot formation, whereas the N-(4-pyridazinyl)-N'-phenylureas of the present invention form shoots in a concentration lower than 1 ppm.

The N-(4-pyridazinyl)-N'-phenylreas in accordance with the invention exhibit a marked weight increase effect not only on tobacco callus cells, but also on pith tissue, leaf tissue or growing plants.

The plant growth regulators of the invention can apply to a wide variety of plants, but are particularly effective for plants belonging to Leguminosae, Solanaceae, Oenanthe, Curcurbitaceae, grapevines, etc.

Where the compounds of the invention are applied to plants, the compounds per se may be added to a carrier medium or they can be applied directly to the plant or onto the surface of leaves or stalks thereof, or sprayed on the soil; they are usually applied in the form of a conventional preparation thereof, such as, a liquid, suspension, emulsion, powder, etc. Further, the plant growth regulators of the invention may be applied together with conventional fertilizers and/or extenders.

The optimal concentration of the compounds of the invention providing the aforesaid activities is determined, needless to say, depending upon its susceptibility of respective plants to chemicals, and one skilled in the art can easily determine a range for the optimal concentration. In addition, the optimal concentration is affected by the time of application, purpose, etc., and it is thus difficult to set forth a range for the optimal concentration covering all application aspects. However, in general, the amount of the compounds of the invention used when they are applied by direct spraying onto the plants is generally about 10 to about 100 liters per 10 area, preferably 0.01 to 10,000 ppm as a solution of a concentration of 0.0001 to 10,000 ppm, as active ingredient. When applied to the soil, an amount of about 5 to about 100 times that given above is required. It goes without saying, however, that the amount applied will differ according to the object of the control and the type of plant involved.

In general, about 10 to about 100 liters of a solution of the following concentration of one or more compounds of the invention as active ingredient(s), is used per 10 ares:

For Growth acceleration and increased fruiting: 0.001–1,000 ppm

For acceleration of fruit falling and defoliation: 10–10,000 ppm

For growth suppression and herbicide use: 10–10,000 ppm

For proliferation of cultured cells (growth acceleration): 0.000001–10 ppm

The compounds of this invention can be used alone or in admixture with other substances or compositions to achieve various effects desired during use, for example, with other plant regulators (auxin, gibberelline, etc.), herbicides (2.4-dichlorophenoxyacetic acid, etc.), insecticides, fugicides and acaricides, typically in the form of a solution, emulsion, wettable powder, granule, fine granule or powder.

The preparation of suitable compositions comprising the compounds of the invention is carried out in a conventional manner, e.g., by mixing 0.1 to 50%, preferably 0.1 to 10%, of a compound or compounds of the invention with a bulking agent, such as a liquid or solid diluent or carrier, and, if desired or necessary, an emulsifying agent or dispersing agent.

Preferred liquid diluents or carriers include water, aromatic hydrocarbons such as xylene, benzene and methylnaphthalene, chlorinated aromatic hydrocarbons such as chlorobenzene, mineral oil fractions such as paraffin, alcohols such as methanol and propanol, and polar solvents such as dimethylformamide, acetone, etc.

Preferred solid diluents or carriers include talc, clay, kaolin, white carbon, wood powder, sand, etc.

Preferred emulsifying agents include polyoxyethylene-fatty acid esters or polyoxyethylene-fatty acid alcohol ethers and preferred dispersing agents include alkyl sulfonates, alkyl aryl sulfonates, alkali metal salts, alkaline earth metal salts, ammonium salts of lignin-sulfonic acid and methyl cellulose.

The compounds of the invention can also be used in the form of an inorganic or organic salt such as the hydrochloride, phosphate, sulfate, citrate or tartarate thereof.

The present invention will now be described in detail with reference to the examples below, but it is not to be deemed limited thereto.

EXAMPLE 1

200 mg. of 4-aminopyridazine was suspended in 50 ml. of acetone. To the resulting suspension, 1.2 times the amount of phenyl isocyanate theoretically calculated was added and the mixture then reacted at room temperature overnight. The crystals formed were taken out by filtration. By recrystallization from an excess of methanol, N-(4-pyridazinyl)-N'-phenylurea was obtained (yield, greater than 80%); melting point higher than 250° C.

Similar results were obtained when 30 ml. of pyridine was used instead of acetone.

Elemental analysis for $C_{11}H_{10}N_4O$

| | C (%) | H (%) | N (%) |
|---|---|---|---|
| Calcd. | 61.68 | 4.67 | 26.17 |
| Found | 61.38 | 4.67 | 25.92 |

EXAMPLE 2

Following the procedure of Example 1, N-(4-pyridazinyl)-N'-(3-chlorophenyl)urea was obtained by reaction in acetone as a solvent (melting point higher than 250° C.).

Elemental analysis for $C_{11}H_9N_4OCl$

|  | C (%) | H (%) | N (%) |
|---|---|---|---|
| Calcd. | 53.12 | 3.62 | 22.54 |
| Found | 53.08 | 3.64 | 21.84 |

EXAMPLE 3

490 mg. of 4-azidocarbonyl-6-chloropyridazine was refluxed for 60 mins. in 50 ml. of benzene. After cooling to room temperature, 248 mg. of aniline was added to the system. The precipitate formed was separated by filtration. The precipitate was recrystallized from a large excess of methanol to obtain 460 mg. of N-(6-chloro-4-pyridazinyl)-N'-phenylurea at a yield of 69%; m.p. 254°–260° C. (decompd.).

Mass spectrum (M+/e): 250, 248.

Elemental analysis for $C_{11}H_9N_4OCl$

|  | C (%) | H (%) | N (%) |
|---|---|---|---|
| Calcd. | 53.13 | 3.65 | 22.53 |
| Found | 53.00 | 3.29 | 22.30 |

EXAMPLE 4

Following the procedure of Example 3, N-(6-chloro-4-pyridazinyl)-N'-(3-chlorophenyl)urea was obtained at a yield of 55%; m.p. 240°–248° C. (decompd.). The starting materials were 4-azidocarbonyl-6-chloropyridazine and 3-chloroaniline.

Mass spectrum (M+/e): 286, 284, 282.

EXAMPLE 5

Following the procedure of Example 3, N-(6-chloro-4-pyridazinyl)-N'-(3-fluorophenyl)urea was obtained using 4-azidocarbonyl-6-chloropyridazine and 3-fluoroaniline; m.p. 293°–296° C. (decompd.).

Mass spectrum (M+/e): 268, 266.

EXAMPLE 6

Tobacco callus cells (about 50 mg.) prepared from the pith tissue of 3 g. of tobacco (Wisconsin) were inoculated in Murashige-Skoog medium containing 2 ppm of indole acetic acid and the system cultured at a temperature of about 26° C. for 30 days, whereafter the weight of the tobacco callus was measured. As a positive control, 6-benzyladenine (referred to as BA: optimal concentration 0.01 ppm) was tested in a similar fashion.

The results are given in Table I below.

TABLE I

| Compound | Concentration (ppm) | Yield of Callus (g.) |
|---|---|---|
| (control) | — | 0.13 |
| BA | 0.01 | 3.69 |
| N—(4-Pyridazinyl)-N'—phenylurea | 0.000001 | 1.34 |
|  | 0.00001 | 2.16 |
|  | 0.0001 | 6.99 |
|  | 0.001 | 4.10 |
|  | 0.01 | 4.67* |
|  | 0.1 | 1.96* |
|  | 1 | 0.87* |
|  | 10 | 0.96* |

*Hard callus characteristic of overdose use:
Formation of stalks and leaves due to cell differentiation was observed.

As can be seen from the results above, proliferation of callus growth was observed at a concentration of 0.001 to 0.00001 ppm; at a concentration exceeding such, the callus growth was suppressed and acceleration of differentiation into stalks and leaves was noted.

In more detail, the concentration which gave the best yield of callus was 0.0001 ppm with the compound of the present invention, about 1/100 that of BA, about 1/1000 that of N-(4-pyridyl)-N'-phenylurea and about 1/10 that of N-(2-chloro-4-pyridyl)-N'-phenylurea. In addition, the callus yield was excellent with the compound of the present invention when compared with BA.

EXAMPLE 7

Test on Increase in Size of Leaves of Green Vegetable Using N-(4-Pyridazinyl)-N'-phenylurea Leaves of *Brassica repa var. pervidis* which had been cut out into round sections with a corkborer (diameter 10 mm., weight 17.0 mg.) were floated on the surface of water containing the above-identified compound at the concentrations below so as to contact the water with the back of the leaf sections. The system was allowed to stand for 8 days at room temperature. Thereafter, the diameter and weight of the leaf sections were determined. The results are shown in Table II below wherein all values are an average of 10 pieces of the leaf sections.

TABLE II

| Concentration (ppm) | Diameter (mm.) | Weight (mg.) |
|---|---|---|
| 10 | 15.0 | 32.0 |
| 1 | 15.3 | 32.0 |
| 0.1 | 17.0 | 35.0 |
| 0.01 | 17.9 | 35.2 |
| 0.001 | 13.5 | 27.0 |
| Control | 12.0 | 24.0 |

As can be seen from the above results, the optimum concentration was 0.01 ppm with the above compound of this invention.

EXAMPLE 8

Test on Increase of Weight and Supression of Height in Datura Sunguinea Using N-(4-Pyridazinyl)-N'-phenylurea Datura Sunguinea sp. (average height: 8 cm.) were transplanted outdoors. When the average height of the plants became 20 cm., an emulsion of the above-identified compound at a concentration as shown in Table III below was sprayed on the plants in an amount of 15 ml. per one plant. Three weeks later, the plants were harvested and the height of the plants and the total weight appearing on the ground were measured. The results are shown in Table III below wherein values are an average of five plants.

TABLE III

| Compound | Concentration (ppm) | Height (cm.) | Total Weight (g.) |
|---|---|---|---|
| Compound of This Invention | 100 | 100 | 403 |
|  | 200 | 98 | 421 |
| 6-Benzyladenine | 500 | 107 | 362 |
| Control (no compound) | — | 110 | 340 |

As can be seen from the results above, the height of the plants became shorter than the control and the total weight of the leaves was greatly increased with the above compound of the invention.

EXAMPLE 9

Activity of N-(4-Pyridazinyl)-N'-phenylurea in the Wheat Leaf Senescenece Test 10 cm. long primary leaves of spring wheat were detached from 10 day-old plants. The leaves were immersed in an aqueous suspension of the above identified compound contained in a test tube at concentrations as indicated in Table IV below [three (3) replicates]. The test tubes were kept in a growth chamber and, as a positive control, kinetin was used at concentrations as indicated in the table below.

The leaf color was visually determined according to a linear rating scale:

1: leaves as dark as at the time of treatment
2–8: increasing discoloration from green to yellow
9: leaves yellow equal to blank control (no compound was added)

TABLE IV

| Concentration (ppm) | Leaf Color Compound of Invention | Kinetin | Blank Control |
|---|---|---|---|
| 0 (no addition) | — | — | 9.0 |
| 1.25 | 1.0 | 3.3 | — |
| 2.5 | 1.0 | 3.0 | — |
| 5.0 | 1.0 | 3.0 | — |

The compound of the invention showed a strong senescene inhibition activity on detached wheat leaves, more intensively than kinetin as a positive control.

While the invention has been described in detail and with reference to specific embodiments thereof, it will be apparent to one skilled in the art that various changes and modifications can be made therein without departing from the spirit and scope thereof.

What is claimed is:

1. An agricultural composition useful as a plant growth regulator comprising as an active ingredient a compound of formula:

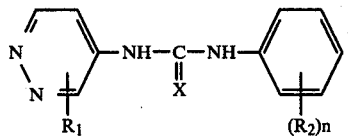

wherein $R_1$ and $R_2$, which may be the same or different, each represents a hydrogen atom, a lower alkyl group, a halogen atom, a lower alkoxy group, an aryloxy group, a halomethyl group, a cyano group, an alkylthio group, a carboxy group or an alkoxycarbonyl group; X represents an oxygen atom or a sulfur atom; and n represents 1, 2 or 3; and when n is 2 or 3, $R_1$ and $R_2$ each may be different, in an effective plant-growth regulating amount, together with an inert carrier or diluent.

2. The agricultural composition of claim 1 wherein said active ingredient is contained in a concentration of about 0.000001 ppm to about 1%.

3. The agricultural composition of claim 1 wherein said active ingredient is selected from N-(4-pyridazinyl)-N'-phenylurea and N-(4-pyridazinyl)-N'-(m-fluorophenyl)urea.

4. A method of controlling plant growth which comprises contacting a plant or a part thereof with a compound of formula:

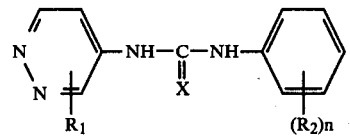

wherein $R_1$ and $R_2$, which may be the same or different, each represents a hydrogen atom, a lower alkyl group, a halogen atom, a lower alkoxy group, an aryloxy group, a halomethyl group, a cyano group, an alkylthio group, a carboxy group or an alkoxycarbonyl group; X represents an oxygen atom or a sulfur atom; and n represents 1, 2 or 3; and when n is 2 or 3, $R_1$ and $R_2$ each may be different, in an amount effective for regulation of the growth of the plant involved.

* * * * *